Aug. 27, 1935. M. LEENDERS Plant Pat. 138
ROSE
Filed April 8, 1935
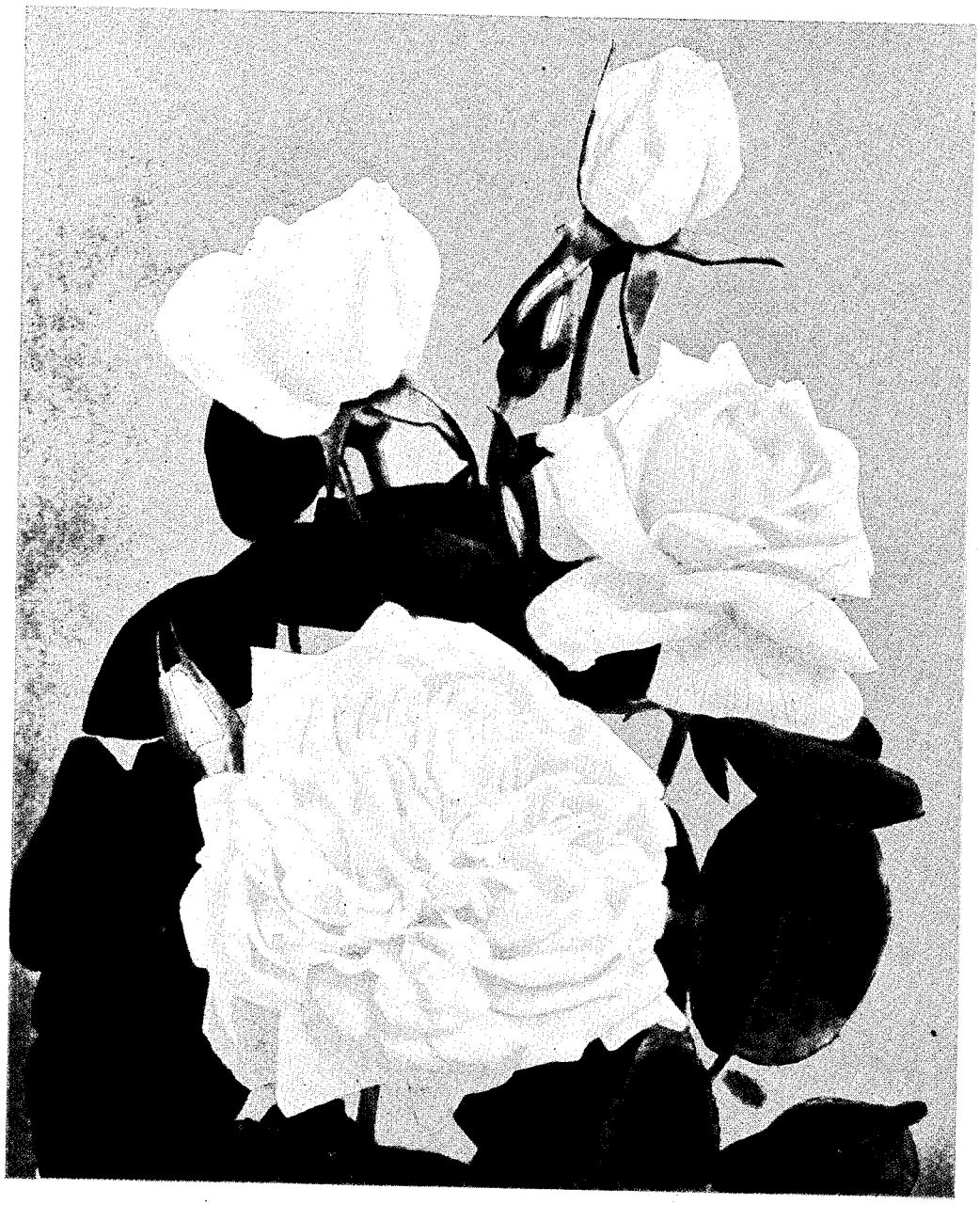
Inventor
Matthias Leenders
By Robb & Robb
Attorneys Patented Aug. 27, 1935

UNITED STATES PATENT OFFICE

138

ROSE

Matthias Leenders, Steyl-Tegelen, Netherlands, assignor to Jackson & Perkins Company, Newark, N. Y.

Application April 8, 1935, Serial No. 15,315

1 Claim. (Cl. 47—61)

The present invention refers to a new and distinct variety of rose plant and had for its definite objective the production of a rose of vigorous habits in which its yellow color would be so reinforced, so to speak, as to be rendered more lasting. This result was successfully accomplished by the crossing of a Tea or Noisette yellow variety with another yellow of the Pernetiana Hybrid Perpetual race.

By bringing together these varieties, as represented specifically by the "Marechal-Niel" and "Mabel Morse" strains of roses, I obtained a bloom which is very large, full and of symmetrical form and the color of which graduates from a pale yellow at the rim of the bloom to a reddish yellow at the center. (All color designations herein are in accord with the Gravereaux system and dictionary definitions.)

It has the strong fragrance of Tea rose inherited from its ancestor Marechal-Niel.

While my new variety is not particularly classed as a florist rose, nevertheless it is very useful as a cut flower type because of its distinctive characteristic of lasting for an unusually long period in water indoors, retaining its color permanently.

Furthermore, the new variety is a garden rose of what is known as the exhibition type, being at the same time very decorative as its large blooms, when fully expanded, some four inches to five inches in diameter, are quite noticeable from a long distance.

It may be noted that by "exhibition" type, I desire it to be understood that garden roses may be subdivided into two classes, exhibition and decorative varieties, and the former is usually a variety producing large, well-formed blooms in limited numbers that are amenable to special treatment, more or less artificial, to bring them to show or exhibition size. Decorative roses, on the other hand, are seldom of exhibition size, but decorative roses ordinarily are the only useful garden rose. In the present invention, I have been able to produce a variety which is a combination of the two types and in this respect the new variety is quite distinctive.

In other words, the new variety is desirable as a garden rose because of the unusual combination of characters that make it useful both for producing exhibition roses and for garden decoration. It is valuable for exhibition because by suitable pinching out of some of the blooms well formed flowers of large size may be developed from the remaining ones, while without such pinching a showy mass effect with smaller blooms is produced that is desirable for garden decoration.

The foliage of this new plant is very large, much larger than the ordinary hybrid tea, and distinctive, having inherited its size and appearance from the Marechal-Niel side of its ancestry.

Asexual reproduction proves the characteristics herein referred to to be permanently fixed.

The following is a detail description of this new variety:

Parentage:
- Seedling.
- Seed parent, Mrs. T. Hillas, a tea rose of Marechal-Niel parentage.
- Pollen parent, Mabel Morse.

Classification:
- *Botanic.*—Pernetiana Hybrid.
- *Commercial.*—Hybrid tea.

*Flower*

Blooming habit:
- Intermittent.

Bud:
- *Size.*—Very large.
- *Form.*—Long, ovoid. Unaffected by wet or hot weather.
- *Color.*—When sepals first divide reddish yellow; when petals begin to unfurl ochre yellow; when half blown; inside of petals gold yellow, reverse of petals clear yellow.
- *Sepals.*—Smooth edge; curl back as soon as bud begins to unfurl.
- *Calyx.*—Shape—funnel. Size—broad. Aspect—smooth. Odor when rubbed—none.
- *Peduncle.*—Length — long. Aspect — smooth. Color—light green. Strength—erect, heavy.
- *Opening.*—Bud opens well and is not affected by adverse conditions.

Bloom:
- *Size.*—Very large. Average size when open 4" to 5".
- *Borne.*—Singly.
- *Stems.*—Medium length; normal strength.
- *Form.*—When first open flat.
- *Permanence.*—Retains its form to the end; outer petals curl back.
- *Petalage.*—Very double (many petals and stamens hidden.) Number of petals under normal conditions 100.
- *Color:* Center of flower—reddish yellow. Outer petals—pale yellow. Base of petals (aiglet)—yellow. Inside of petals—yellow. Reverse of petals—same yellow. General tonality from a distance—lemon yellow with deeper center.

*Variegations.*—None.
*Discoloration.*—General tonality at end of first day deep yellow; second day same; third day paler yellow on outside petals but same inside.

Petals:
*Texture.*—Leathery, soft; unaffected by hot weather but may ball in wet weather.
*Appearance.*—Inside satiny; outside satiny.
*Form.*—Round.
*Arrangement.*—Irregular; quartered sometimes. Petaloids in center—many, small.
*Persistence.*—Hang on and dry.
*Fragrance.*—Tea (average hybrid tea scent).
*Lasting quality.*—On the plant and as a cut flower—very long.

Genital organs:
*Stamens, anthers.*—Medium size, few. Color—yellow. Arrangement—mixed with petaloids.
*Stamens, filaments (threads).*—Medium length. Color—white.
*Pollen.*—Lemon yellow.
*Styles.*—Bunched, uneven length, heavy.
*Stigmas.*—Color—white.
*Ovaries.*—Some protruding from calyx.

Fruit:
Variety may be fertile with its own pollen but have neven seen any fruit.

*Plant*

Form:
Bush.

Growth:
Medium, branching, compact.

Foliage:
Generally five leaflets.
*Size.*—Very large.
*Quantity.*—Normal.
*Color.*—New foliage—upper side normal green, bronzy, under side reddish. Old foliage—upper side light green and under side lighter green.
*Shape.*—Oval, lanceolate.
*Texture.*—Upper side leathery, glossy, flat.
*Edge.*—Serrated (saw toothed).
*Serration.*—Single, small.
*Leaf stem.*—Color reddish; underside prickles.
*Stipules.*—Medium length, smooth.
*Disease resistance.*—Resistant.

Wood:
*New wood.*—Color reddish; bark smooth.
*Old wood.*—Color green; bark smooth.

Thorns: (divided into thorns, prickles and short needles).
*Thorns.*—Quantity—on main stalks from base ordinary. On laterals from stalk few. Form—broad base. Color—when young red. Position—irregular.
*Prickles.*—Quantity—on main stalks none. On laterals none.
*Short needles.*—Quantity—on main stalks none. On laterals none.

I claim:
A new and distinct variety of rose plant as shown and described, characterized as to novelty by the large size exhibition type of bloom and the non-fading yellow color, distinct among yellow roses.

MATTHIAS LEENDERS.